(12) United States Patent
Ragg

(10) Patent No.: US 11,536,278 B2
(45) Date of Patent: Dec. 27, 2022

(54) BLOWER UNIT

(71) Applicant: EBM-PAPST ST. GEORGEN GMBH & CO. KG, St. Georgen (DE)

(72) Inventor: Peter Ragg, Schönwald (DE)

(73) Assignee: EBM-PAPST ST. GEORGEN GMBH & CO. KG, St. Georgen (DE)

( * ) Notice: Subject to any disclaimer, the term of this patent is extended or adjusted under 35 U.S.C. 154(b) by 114 days.

(21) Appl. No.: 15/762,006

(22) PCT Filed: Sep. 21, 2016

(86) PCT No.: PCT/EP2016/001574
§ 371 (c)(1),
(2) Date: Mar. 21, 2018

(87) PCT Pub. No.: WO2017/050427
PCT Pub. Date: Mar. 30, 2017

(65) Prior Publication Data
US 2018/0274545 A1 Sep. 27, 2018

(30) Foreign Application Priority Data
Sep. 24, 2015 (DE) .................... 10 2015 012 277.0

(51) Int. Cl.
*F04D 17/16* (2006.01)
*F04D 25/08* (2006.01)
(Continued)

(52) U.S. Cl.
CPC ......... *F04D 17/16* (2013.01); *A61M 16/0066* (2013.01); *F04D 25/06* (2013.01);
(Continued)

(58) Field of Classification Search
CPC ...... F04D 17/06; F04D 17/16; F04D 25/0606; F04D 25/082; F04D 29/083; F04D 29/5806; F04D 29/668
See application file for complete search history.

(56) References Cited

U.S. PATENT DOCUMENTS

| 2,316,608 A | 4/1943 | McMahan |
| 3,199,774 A | 8/1965 | Lowell |

(Continued)

FOREIGN PATENT DOCUMENTS

| DE | 102007010051 | 9/2008 |
| DE | 102011121149 | 6/2013 |

(Continued)

OTHER PUBLICATIONS

International Search Report for PCT Application PCT/EP2016/001574, dated Dec. 16, 2016 EPO.

*Primary Examiner* — David E Sosnowski
*Assistant Examiner* — Aye S Htay
(74) *Attorney, Agent, or Firm* — Preti Flaherty Beliveau & Pachios LLP

(57) ABSTRACT

A blower unit, particularly for an apparatus for assisting respiration, comprises a housing (2), an impeller (1) accommodated in an impeller chamber (3) in the housing (2), and a motor (12), connected to the impeller (1) via a shaft (15), which is accommodated in a motor chamber (13) in the housing (2). The motor (12) is fixed between walls (14, 18) of the motor chamber (13) by means of buffers, with at least one of the buffers being a sealing ring (16) which separates the shaft (15) from a passage for cooling air (33) which, in radial section, extends annularly around the motor (12).

13 Claims, 3 Drawing Sheets

(51) Int. Cl.
  *F04D 29/08* (2006.01)
  *F04D 29/58* (2006.01)
  *F04D 25/06* (2006.01)
  *A61M 16/00* (2006.01)
  *F04D 29/66* (2006.01)

(52) U.S. Cl.
  CPC ....... *F04D 25/0606* (2013.01); *F04D 25/082* (2013.01); *F04D 29/083* (2013.01); *F04D 29/5806* (2013.01); *F04D 29/668* (2013.01); *F05D 2240/55* (2013.01)

(56) References Cited

U.S. PATENT DOCUMENTS

| | | | | |
|---|---|---|---|---|
| 4,111,615 A | * | 9/1978 | Watanabe | A47L 5/22 |
| | | | | 415/119 |
| 4,783,608 A | * | 11/1988 | Gruber | H02K 5/1675 |
| | | | | 310/43 |
| 5,743,721 A | * | 4/1998 | Graham | F04D 25/082 |
| | | | | 310/58 |
| 6,034,451 A | * | 3/2000 | El Mayas | F04D 25/082 |
| | | | | 310/58 |
| 6,079,958 A | * | 6/2000 | Qandil | F04D 13/08 |
| | | | | 416/204 R |
| 6,177,741 B1 | * | 1/2001 | Lutkenhaus | H02K 3/47 |
| | | | | 310/71 |
| 8,267,674 B2 | * | 9/2012 | Czulak | F04D 29/584 |
| | | | | 417/370 |
| 9,074,604 B2 | * | 7/2015 | Konishi | F04D 17/164 |
| 2010/0189554 A1 | | 7/2010 | Grasmuck | |
| 2012/0275915 A1 | * | 11/2012 | Konishi et al. | |
| 2014/0014109 A1 | * | 1/2014 | Grasmuck | A61M 16/0066 |
| | | | | 128/204.18 |
| 2017/0102003 A1 | * | 4/2017 | Sishtla | F04D 17/122 |

FOREIGN PATENT DOCUMENTS

| | | |
|---|---|---|
| EP | 1688622 | 8/2006 |
| WO | 2103187786 | 12/2013 |

* cited by examiner

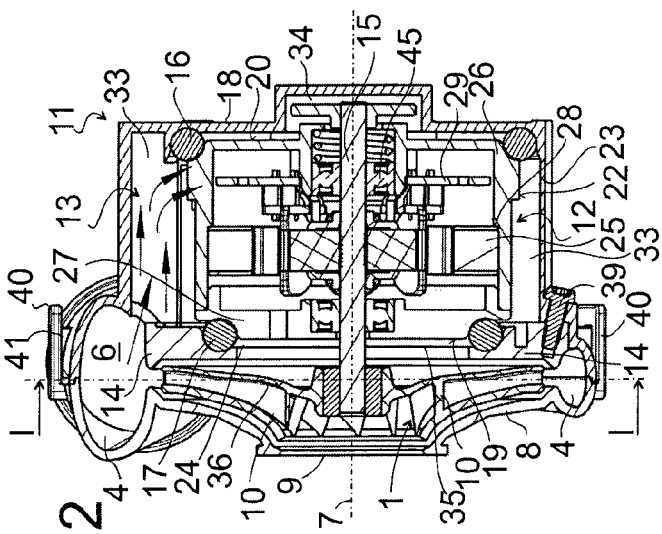
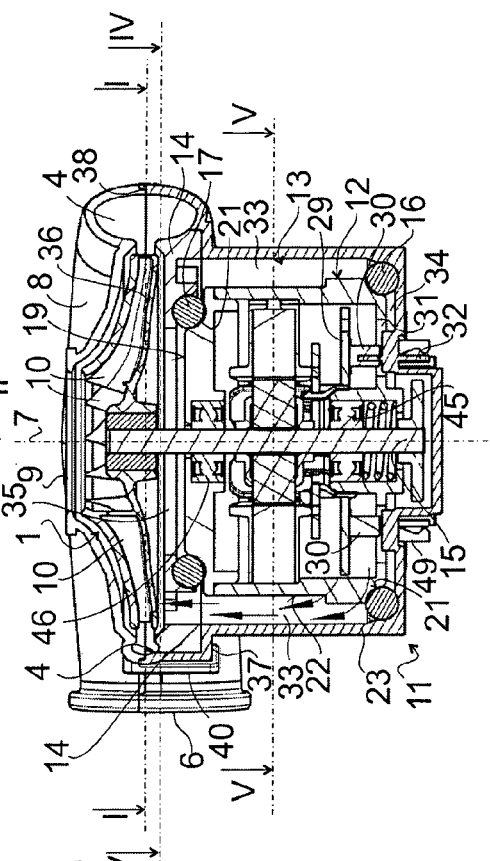
Fig. 1
Fig. 2
Fig. 3

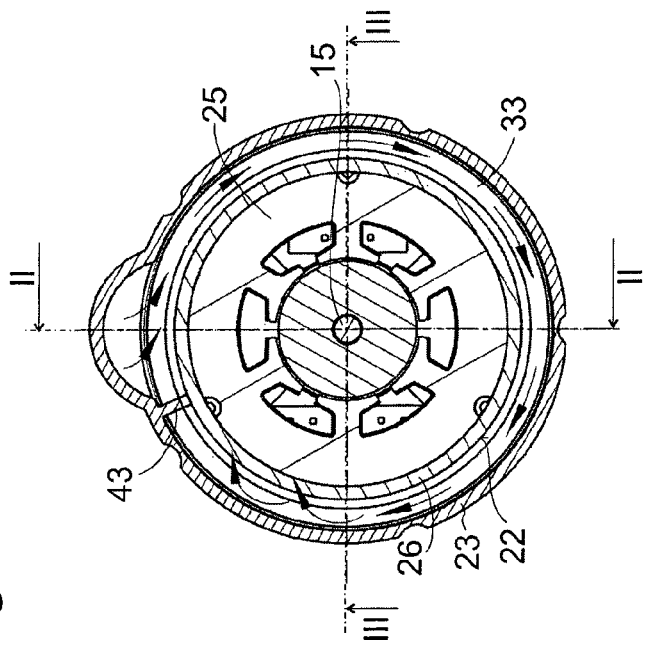
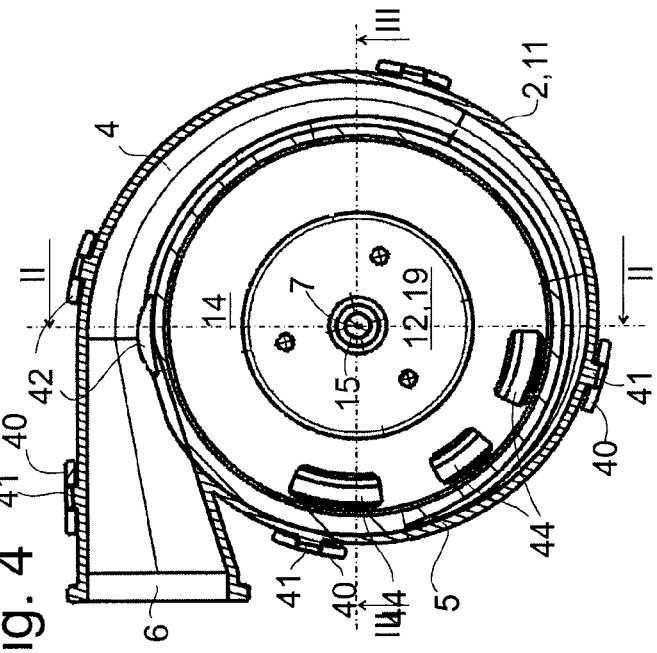

BLOWER UNIT

TECHNICAL FIELD

The present invention relates to a blower unit having a housing, an impeller accommodated in an impeller chamber in the housing, and a motor, connected to the impeller via a shaft, which is accommodated in a motor chamber in the housing.

BACKGROUND INFORMATION

Known from U.S. Pat. No. 8,267,674 B2 is a blower unit of this kind in which, to cool the motor, through-openings are so arranged between the impeller chamber and motor chamber that rotation of the impeller also drives a flow of air through the motor chamber.

In this known blower unit, the cooling air is passed directly through the motor which, though it makes efficient cooling possible, at the same time involves the risk that as it passes through the motor the air will pick up odors when in contact with windings which have heated up in operation and with surfaces covered in lubricant, and these odors will mix with the circulated air in the impeller chamber and will still be perceptible in the flow of blown air from the blower unit.

The motor is fixed into the motor chamber by being in direct contact with the walls thereof. Vibration from the motor may therefore be transmitted undamped to the walls of the housing and may excite these to emit noise.

In the case of a blower unit which, as specified in U.S. Pat. No. 826,764 B2, is intended for motor vehicle applications, the noise caused by the operation of the blower unit is insignificant in comparison with that of an internal combustion engine which is operated at the same time, and even any undesirable odors which may exist are hardly perceived over other, stronger, odors from the road traffic. In a blower unit which is intended for medical applications such as, say, a unit for assisting respiration, low-noise operation and freedom of the blown air from unwanted odors is of incomparably greater importance.

It is therefore an object of the invention to create a blower unit which both makes low-noise operation possible and also prevents the blown air from being contaminated by odors in an effective way.

In a blower unit having a housing, an impeller accommodated in an impeller chamber in the housing, and a motor, connected to the impeller via a shaft, which is accommodated in a motor chamber in the housing, this object is achieved by fixing the motor between walls of the motor chamber by means of buffers, with at least one of the buffers being a sealing ring which separates the shaft from a passage for cooling air which, in radial section, extends annularly around the motor. The fixing by means of buffers at two ends of the motor allows direct contact by the motor with the walls of the housing to be prevented, and hence transmission of vibration of the motor to the housing to be permitted in, at most, a form damped by the buffers, which notably reduces the noise emitted via the housing. By having at least one of the buffers take the form of a sealing ring, this sealing ring prevents the spread of odors, which may originate in particular from a bearing of the shaft in the motor, into the air circulating through the passage for cooling air.

For this purpose, the inside diameter of the sealing ring should be larger than the outside diameter of a gap between parts of the bearing which rotate against one another.

The buffers may be self-contained components which, like the motor, are inserted in the housing when the blower unit is being assembled. Preferably, to simplify the assembly of the blower unit, they are connected to the housing by multi-component injection molding to create a unit structure.

The walls between which the motor is held by the buffers are preferably spaced apart in the direction of the shaft; this simplifies the assembly of the blower unit.

If not just one but two sealing rings are provided, the passage for cooling air may be bounded by the sealing rings, by an outer surface of the motor which extends between the sealing rings, and by an inner surface of the housing which extends between the sealing rings.

The outer surface of the motor which adjoins the passage for cooling air is preferably formed by a stator assembly. Via the metal of the latter, heat from the windings of the motor can be efficiently dissipated and transmitted to the air in the passage for cooling air, without there being any risk of contamination by odors. If the stator assembly is not exposed but is enclosed within the motor housing, then the wall of the latter should at least rest directly against the stator assembly in order to facilitate the outflow of heat to the passage for cooling air.

To ensure efficient cooling even when the throughput of air through the passage for cooling air is low, the annular passage for cooling air may be interrupted at one point by a dividing wall, and an inlet to and an outlet from the passage for cooling air are arranged adjacent the dividing wall on different sides thereof to compel the cooling air to flow round the motor in a circumferential direction and to pick up the heat from it in this way.

Of the inlet to and outlet from the passage for cooling air at least one should be connected to the impeller chamber.

If in particular the inlet to the passage for cooling air comes off a passage for blown air which extends round the impeller, a pressure above atmospheric prevailing in the passage for blown air can be used to drive circulation through the passage for cooling air.

The outlet from the passage for cooling air should preferably open again into the impeller chamber so that the air flowing through the passage for cooling air is not lost from the flow of blown air from the blower unit.

The throughput of air through the passage for blown air increases continuously from an inner end to an outer end at which the exit opening for the flow of blown air is situated. In order to make use of a pressure differential which exists between the ends of the passage for blown air to drive the flow of cooling air, one of the inlet to and outlet from the passage for cooling air should come off the passage for blown air adjacent the inner end and the other should come off it adjacent the outer end.

The housing of the blower unit is generally assembled from a plurality of parts. In particular, a first housing part which receives the motor and a second housing part which comprises an intake opening may adjoin one another in an outer wall of the passage for blown air.

The first and second housing parts are preferably connected together by latching hooks.

An intermediate wall between the motor and impeller chambers is preferably fastened, and in particular screwed or bolted, to the first housing part. An advantage of this construction is on the one hand that, because the intermediate wall is enclosed within the housing, no blown air can be lost along its edges from the housing and because of this the intermediate wall does not need to be connected at its edges to the first housing part with a seal to prevent any losses of air. Further by having the fastening accomplished by screwing or bolting, the clamping of the motor between the buffers can be set.

A pin connector, which is used at least for the supply of current to the motor but which can also be used for the transmission of control signals to the motor or of sensor signals to an external control unit, is preferably injection molded into a wall of the housing in such a way as to be sealed therein.

Other features and advantages of the invention can be seen from the following description of embodiments which is given by reference to the accompanying drawings. In the drawings:

FIG. 1 is a radial section through a blower unit according to the invention taken on a plane which is indicated by I-I in each of FIGS. 2 and 3;

FIG. 2 is an axial section through the blower unit taken on a plane which is indicated by II-II in FIG. 1;

FIG. 3 is an axial section taken on a plane indicated by III-III in FIG. 1 which is orthogonal to the plane II-II;

FIG. 4 is an axial section through the blower unit taken on a plane which is indicated by IV-IV in FIG. 3;

FIG. 5 is an axial section through the blower unit taken on a plane which is indicated by V-V in FIG. 3;

DETAILED DESCRIPTION OF THE PREFERRED EMBODIMENTS

Figure 8:
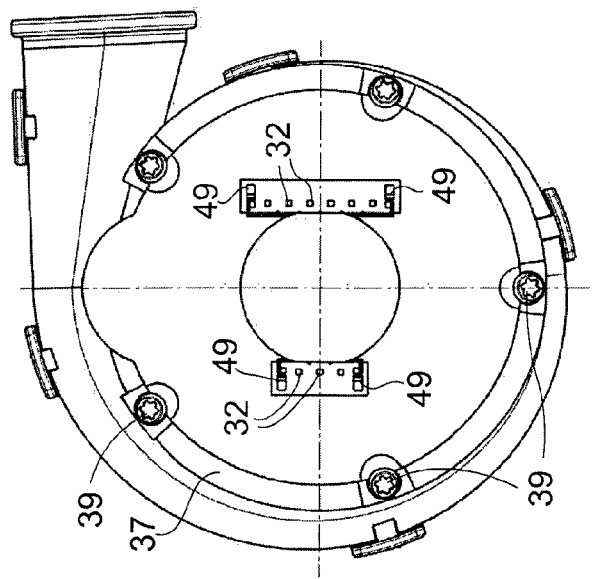
FIG. 8 is a view of the blower unit from below.

FIG. 1 is a radial section through the blower unit according to the invention taken at the point where an impeller 1 is situated. Formed in a housing 2 which is assembled from a plurality of injection moldings of plastics material is an impeller chamber 3 of which the impeller 1 occupies a central region. Extending in a ring round the central region is a passage for blown air 4 whose dimensions in cross-section relative to an axis of rotation 7 of the impeller 1 increase continuously both in the radial and the axial directions from a starting point 5 to, moving counter-clockwise, an end point at an exit opening 6.

Figure 6:
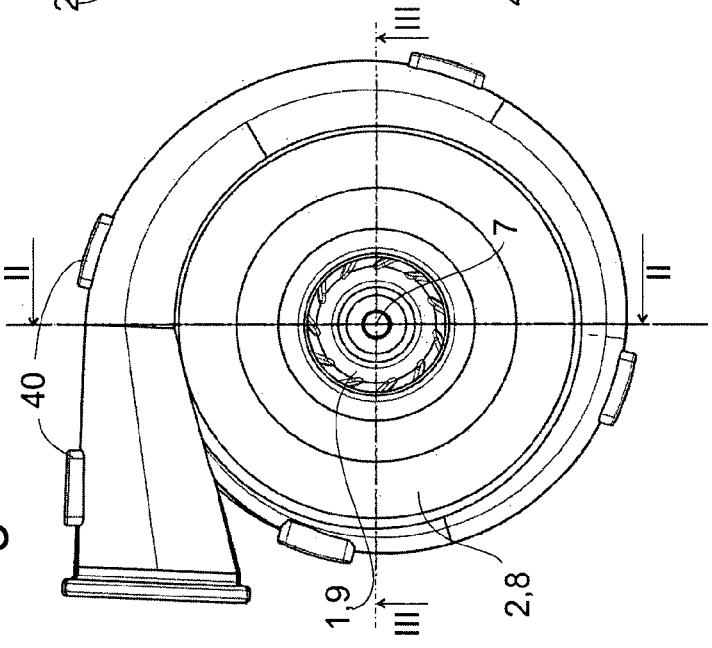
FIG. 6 is a plan view of the blower unit.

As can be seen in the sections in FIGS. 2 and 3 and in the plan view in FIG. 6, an intake opening 9 is formed in a top part 8 of the housing 2 on a continuation of the axis of rotation 7 of the impeller 1. Air which enters the housing 2 via the intake opening 9 is accelerated outwards radially by the blades 10 of the impeller 1, which rotate counter-clockwise, and is impelled towards the exit opening 6 in the passage for blown air 4.

A motor chamber 13 in which an electric motor 12 is accommodated is formed in a cup-shaped bottom part 11 of the housing 2. An intermediate wall 14 in the form of a housing component separate from the top part 8 and bottom part 11 separates the motor chamber 13 from the impeller chamber 3. A shaft 15 of the electric motor 12 projects through an opening in the intermediate wall 14 and into the impeller chamber 3 to carry the impeller 1.

The motor 12 has a substantially cylindrical body and is fixed in position in the motor chamber 13 with the help of two elastic sealing rings 16, 17 which are clamped between respective end faces 20, 19 of the cylindrical body and, respectively, a bottom plate 18 of the housing bottom part 11 and the intermediate wall 14. In the case shown here, the sealing rings 16, 17 at the same time fix the motor 12 in position in the radial direction as well, which they do by engaging with the motor 12 at respective grooves 21 at the transitions between the end faces 20 and 19 respectively and a circumferential surface 22 of the cylindrical body, and, on the other hand, by being respectively supported against a wall 23 of the bottom part 11 which runs in a loop round the bottom plate 18, and against the inner face of a recess 24 in the intermediate wall 14 which is open towards the motor 12.

The sealing rings 16, 17 may be components separate from the bottom part 11 and intermediate wall 14 respectively which are fitted on when the blower unit is being assembled. The sealing ring 16 and the bottom part 11 or the sealing 17 and the intermediate wall 14 are preferably connected even before assembly by molding the sealing ring onto the bottom part 11 or the intermediate wall by multi-component injection molding or, the other way round, by inserting a sealing ring in the injection mold for the bottom part 11 or the intermediate wall and molding these latter onto the sealing ring.

The circumferential surface 22 could be formed directly by a stator assembly of the motor; in the case considered here, the stator assembly 25 is enclosed in a housing which is assembled from two inter-engaging shell-parts, a cup 26 and a cover 27, one of which forms the end face 20 and the other of which forms the end face 19, and the circumferential surface 22 is formed substantially by the outside of a circumferentially extending wall of the cup 26. A shoulder 28 is formed on the inside of this circumferentially extending wall. Accommodated between the shoulder 28 and the floor of the cup 26 is a printed circuit board 29 for electronics which is supplied with energy via sockets 30 (see FIG. 3). Respective openings 31 in the end face 20 are situated opposite the sockets 30, meaning that contact pins 32 anchored in the bottom plate 18 of the housing bottom part 11 can engage in the sockets 30 of the printed circuit board 29 for electronics without coming into contact with the housing of the motor 12. Vibration which is excited in the cup 26 by the movement in rotation is therefore transmitted to the housing bottom part 11 via the contact pins 32 in at most a form which is severely damped by the printed circuit board 29 for electronics.

Figure 9:
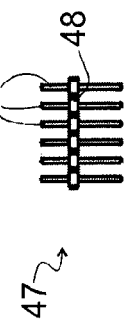
FIG. 9 shows a pin connector of the blower unit.

The anchoring of the contact pins 32 in the bottom plate 18 is achieved by mounting in an injection mold a pin connector 47, of a type known per se (see FIG. 9) in which the contact pins 32 are embedded in a narrow bar of plastics material 48, and injection molding the housing bottom part 11 onto the bar 48. The plastics material from which the housing bottom part 11 is injection molded is preferably the same as that of the bar 48, thus causing the latter to be melted into one piece with the bottom plate 18 in the course of the injection molding. Latching hooks 49 integrally formed on the outside of the bottom plate 18 adjacent the contact pins 32 (see also FIG. 8) serve to anchor in place by positive inter-engagement a plug (not shown) on a supply cable.

The stator assembly 25 is slid into the cup 26 until it reaches the shoulder 28, and is in frictional contact over a wide area with the inside face of the surrounding wall, waste heat from the stator assembly 25 thus being conducted away to the circumferential surface 22.

The sealing rings 16, 17 divide the motor chamber 13 into a passage for cooling air 33, which extends between the circumferential surface 22 of the motor 12 and the wall 23 of the housing bottom part 11 and which is bounded in the axial direction by the sealing rings 16, 17, a space 34 between the bottom plate 18 and the end face 20, situated opposite, of the motor 12, and a space 35 between the end face 19 of the motor 12 and the intermediate wall 14. In the case considered here, the intermediate wall 14 contains a large opening via which the space 35 is connected to a lower region of the impeller chamber 3 which is bounded by a bottom plate 36 of the impeller 1.

As can best be seen from FIG. 3, the bottom part 11 is widened radially into a flange 37 around the top edge of the wall 23, to form a recess which fits round the intermediate wall 14 in a ring and, above the intermediate wall 14, a lower part of the impeller chamber 2. The bottom half of the passage for blown air 4 is bounded partly by the intermediate wall 14 and partly by the housing bottom part 11. Edges of the housing top and bottom parts 8 and 11 meet one another in the plane I-I, the intermediate wall 14 thus being entirely concealed within the housing 2. The edges are of stepped outlines complementary to one another which engage in one another to make a substantially airtight seal.

Figure 7:
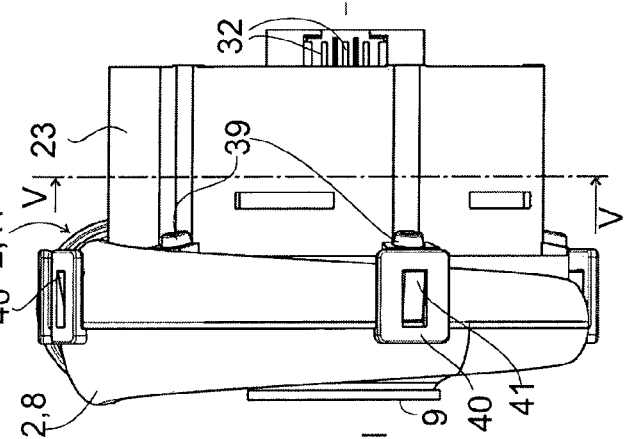
FIG. 7 is a view from the side.

What are used to fasten the intermediate wall in place are a plurality of screws or bolts 39 (see also FIGS. 7, 8) which, as shown in FIG. 2, engage in an approximately axial direction through the flange 37 in threads in the intermediate wall 14, so that the sealing rings 16, 17 are compressed in the axial direction between, respectively, the motor 12 and the bottom plate 18, and the motor 12 and the intermediate wall 14, by tightening the screws or bolts 39.

The motor 12 is thus fixed in place in the motor chamber 13, by the sealing rings 16, 17 alone, in a position in which there is no direct contact between the motor 12 and the walls 23, 18 of the motor chamber 13. Vibration which the motor causes in operation is therefore transmitted to the housing substantially only via the sealing rings 16, 17 and is damped when so transmitted.

The top and bottom parts 8, 11 of the housing 2 are held together by latching and in the present case with the help of flexible elastic latching hooks 40 on the top part 8, which are pushed onto noses for latching 41 on the housing bottom part 11.

The plane on which the section in FIG. 2 is taken intersects the passage for blown air 4 shortly before the exit opening 6. Between the wall 23 and the intermediate wall 14, is an inlet 42 is cut out through which air can flow out of the passage for blown air and can penetrate into the passage for cooling air 33 of the motor chamber 13. As can be seen from FIG. 5, there is formed on the wall 23, adjacent the inlet 42, a dividing wall 43 which extends inwards radially as far as the circumferential surface 22 of the motor 12.

The plane IV-IV on which the section in FIG. 4 is taken is situated below the impeller 1. As is clear from this figure in particular, there is formed in the intermediate wall 14, on the opposite side of the dividing wall 43 from the inlet 42, an outlet 44, which takes the form in the present case of a plurality of openings distributed along the edge of the intermediate wall 14. The dividing wall 43 compels the air which has made its way into the passage for cooling air 33 via the inlet 42 to flow in a ring round the motor 12 to the outlet 44 in the opposite direction from the direction of rotation of the impeller 1.

As can be seen from FIG. 3, the outlet 44 opens into the impeller chamber 3 under the edge of the bottom plate 18 and, due to the rotation of the bottom plate 18 and due to the flow of air driven by the impeller 1 which travels into the passage for blown air 4 radially on a level with the blades 10, it is subject to a dynamic pressure below atmospheric which promotes circulation through the passage for cooling air 33.

The space 34 is sealed off hermetically from the air circulating in the passage for cooling air 33 by the sealing ring 16. Odors which are released from lubricant which is used in the motor 12, and in particular in a rolling bearing 45 adjacent the space 34, or from current-carrying parts of the motor 12 in the state where they are warm in operation, cannot escape from the space 34.

It is true that the space 35 is not sealed off hermetically from the impeller chamber 3 in the embodiment shown here but nevertheless no odors make their way into the stream of blown air even from there because, between the space 35 and an adjacent rolling bearing 46, the shaft 15 extends through a tight-fitting opening in the cover 27 which does not allow any exchange of air worth mentioning between the interior of the motor 12 and the space 35.

If as an alternative the motor used is one whose rolling bearing adjacent the impeller is not screened off in the motor housing in the way shown, the opening in the intermediate wall 14 through which the shaft 15 extends can, in a similar way to the opening in the cover 27, be made so tight-fitting that, even though odoriferous substances from the rolling bearing 46 spread into the space 35 between the intermediate wall 14 and the end face 19, they are not able to penetrate in any appreciable quantities from there into the impeller chamber 2.

REFERENCE NUMERALS

1 Impeller
2 Housing
3 Impeller chamber
4 Passage for blown air
5 Starting point
6 End point/Exit opening
7 Axis of rotation
8 Top part
9 Intake opening
10 Blade
11 Bottom part
12 Electric motor
13 Motor chamber
14 Intermediate wall
15 Shaft
16 Sealing ring
17 Sealing ring
18 Bottom plate
19 End face
20 End face
21 Groove
22 Circumferential surface
23 Wall
24 Recess
25 Stator assembly
26 Cup
27 Cover
28 Shoulder
29 Printed circuit board for electronics
30 Sockets
31 Opening
32 Contact pin
33 Passage for cooling air
34 Space
35 Space
36 Bottom plate
37 Flange
38 Stepped outline
39 Screw or bolt
40 Latching hook
41 Nose for latching
42 Inlet 43 Dividing wall
44 Outlet
45 Rolling bearing
46 Rolling bearing
47 Pin connector
48 Bar
49 Latching hook Modification and substitutions by one of ordinary skill in the art are considered to be within the scope of the present invention, which is not to be limited except by the allowed claims and their legal equivalent.

The invention claimed is:

1. A blower unit having a housing (2), an impeller (1) accommodated in an impeller chamber (3) in the housing (2), and a motor (12) having a substantially cylindrical body, connected to the impeller (1) via a shaft (15), wherein said motor (12) is disposed in a motor chamber (13) in the housing (2), characterized in that the motor (12) is fixed between walls (14, 18) of the motor chamber (13) by means of one or more buffers, wherein the one or more buffers comprise two sealing rings (16, 17), said two sealing rings (16, 17) disposed between respective end faces (20, 19) of the cylindrical body of said motor (12) and, respectively, said walls (14, 18) of the motor chamber (13), and wherein the two sealing rings (16, 17) separate the motor (12) and the shaft (15) from an annular passage for cooling air (33), said annular passage for cooling air (33) formed between an outer circumferential surface (22) of the motor (12) and a wall (23) of a motor housing bottom part (11), wherein said annular passage for cooling air (33) extends annularly substantially completely around said outer circumferential surface (22) of the motor (12), wherein said one or more buffers are configured for preventing cooling air from the annular passage for cooling air (33) from entering an interior region of said motor (12), wherein the annular passage for cooling air (33) extending annularly substantially completely around said outer circumferential surface (22) of the motor (12) is interrupted at only one point by a dividing wall (43) extending in a radial direction from said wall (23) of the motor housing bottom part (11) to said outer circumferential surface (22) of the motor (12), and wherein an air inlet (42) and an air outlet (44) from the annular passage for cooling air (33) are arranged adjacent the dividing wall (43) on different sides thereof and configured for providing cooling air from said annular passage for cooling air (33) around an exterior region of said motor (12), and wherein the annular passage for cooling air (33) is bounded by the two sealing rings (16, 17), by the outer circumferential surface (22) of the motor which extends between the two sealing rings (16, 17), and by the wall (23) of the motor housing bottom part (11) of the housing (2) which extends between the two sealing rings (16, 17).

2. The blower unit according to claim 1, characterized in that an inside diameter of one of the two the sealing rings (16, 17) is larger than an outside diameter of a corresponding bearing (45, 46) disposed on the shaft (15), wherein the corresponding bearing (45, 46) and the shaft (15) rotate against one another.

3. The blower unit according to claim 1, characterized in that the walls (14, 18) of the motor chamber (13) are spaced apart in a longitudinal direction of the shaft (15).

4. The blower unit according to claim 1, characterized in that the outer circumferential surface (22) of the motor (12) is formed by a stator assembly (25) or by a circumferentially extending wall of cup (26) which rests tightly against the stator assembly (25).

5. The blower unit according to claim 1, characterized in that at least one of the inlet (42) and the outlet (44) is connected to the impeller chamber (3).

6. The blower unit according to claim 5, characterized in that the impeller chamber (3) comprises a passage for blown air (4) which extends round the impeller (1), and in that at least the inlet (42) to the annular passage for cooling air (33) comes off the passage for blown air (4).

7. The blower unit according to claim 6, characterized in that the throughput of air through the passage for blown air (4) increases continuously from an inner end (5) to an outer end (6) and wherein in one of the inlet and outlet (42, 44) comes off the passage for blown air (4) adjacent the inner end (5) and the other of the inlet and outlet (42, 44) comes off the passage for blown air (4) adjacent the outer end (6).

8. The blower unit according to claim 6, characterized in that the housing (2) comprises said motor housing bottom part (11) which receives the motor (12) and a second housing part (8) having an intake opening (9), wherein said motor housing bottom part and said second housing part adjoin one another in an outer wall of the passage for blown air (4).

9. The blower unit according to claim 8, characterized in that the motor housing bottom part (11) and the second housing part (8) are connected together by latching hooks (40).

10. The blower unit according to claim 8, characterized in that the motor housing bottom part (11) and the second housing part (8) have outlines (38) which engage in one another frictionally.

11. The blower unit according to claim 8, characterized in that the housing (2) also comprises an intermediate wall (14) between the motor chamber (13) and the impeller chamber (3) which is screwed or bolted to the motor housing bottom part (11).

12. The blower unit according to claim 1, characterized in that a pin connector (47) configured for supplying of current to the motor (12) is injection molded into a wall (18) of the housing (2).

13. The blower unit of claim 1, wherein said blower unit is configured to form part of an apparatus for assisting respiration.

* * * * *